United States Patent
Carvajal Alcaraz et al.

(10) Patent No.: US 9,138,487 B2
(45) Date of Patent: Sep. 22, 2015

(54) PROCESS OF PREPARATION AND USES OF PLASMA MEMBRANE VESICLES EXTRACTED FROM PLANTS ENRICHED IN MEMBRANE TRANSPORT PROTEINS

(75) Inventors: Micaela Carvajal Alcaraz, Murcia (ES); Cristina Garcia Viguera, Murcia (ES); Diego Angel Moreno Fernandez, Murcia (ES); Maria del Carmen Martinez Ballesta, Murcia (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 0 days.

(21) Appl. No.: 14/119,497

(22) PCT Filed: May 22, 2012

(86) PCT No.: PCT/ES2012/070366
§ 371 (c)(1),
(2), (4) Date: Feb. 27, 2014

(87) PCT Pub. No.: WO2012/160232
PCT Pub. Date: Nov. 29, 2012

(65) Prior Publication Data
US 2014/0161874 A1    Jun. 12, 2014

(30) Foreign Application Priority Data

May 23, 2011    (ES) .................................. 201130830

(51) Int. Cl.
| | | |
|---|---|---|
| *A61K 36/31* | (2006.01) | |
| *A61K 9/127* | (2006.01) | |
| *A61K 47/48* | (2006.01) | |
| *A23L 2/52* | (2006.01) | |
| *A23L 2/66* | (2006.01) | |
| *A61K 8/14* | (2006.01) | |
| *A61Q 19/00* | (2006.01) | |
| *A61K 8/97* | (2006.01) | |
| *A61K 9/50* | (2006.01) | |

(52) U.S. Cl.
CPC ............. *A61K 47/48815* (2013.01); *A23L 2/52* (2013.01); *A23L 2/66* (2013.01); *A61K 8/14* (2013.01); *A61K 8/97* (2013.01); *A61K 36/31* (2013.01); *A61Q 19/007* (2013.01); *A61K 9/5068* (2013.01); *A61K 2236/00* (2013.01); *A61K 2236/11* (2013.01)

(58) Field of Classification Search
None
See application file for complete search history.

(56) References Cited

PUBLICATIONS

International Search Report issued Sep. 10, 2012 in International (PCT) Application No. PCT/ES2012/070366.
Lopez-Perez et al., "Changes in plasma membrane lipids, aquaporins and proton pump of broccoli roots, as an adaptation mechanism to salinity", Phytochemistry, vol. 70, 2009, pp. 492-500.
Martinez-Ballesta et al., "Two different effects of calcium on aquaporins in salinity-stressed pepper plants", Planta, vol. 228, 2008, pp. 15-25.
Muries et al., "Identification and differential induction of the expression of aquaporins by salinity in broccoli plants", Molecular BioSystems, vol. 7, 2011, pp. 1322-1335.

*Primary Examiner* — Chris R Tate
*Assistant Examiner* — Russell Fiebig
(74) *Attorney, Agent, or Firm* — Wenderoth, Lind & Ponack, L.L.P.

(57) ABSTRACT

The invention relates to a method for obtaining membrane vesicles enriched in membrane transport proteins of plant origin, for cosmetic or therapeutic use, which can contain other substances, such as natural bioactive compounds. Preferably, said vesicles are obtained from plants of the Brassicaceae (cruciferae) family. In addition, the invention relates to a method for increasing these proteins of plant origin.

4 Claims, 9 Drawing Sheets

Control Elicitation

Figure 1:
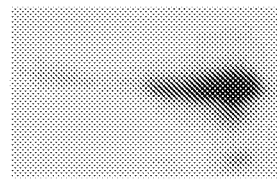

PROCESS OF PREPARATION AND USES OF PLASMA MEMBRANE VESICLES EXTRACTED FROM PLANTS ENRICHED IN MEMBRANE TRANSPORT PROTEINS

FIELD OF THE ART

The present invention scope with chemistry and pharmacology sector, and specifically relates to plasma membrane vesicles enriched in natural intrinsic membrane proteins for application in dermatology, pharmacology or therapeutic.

STATE OF THE ART

In animal cells, the plasma membrane proteins (MP) represent a strategic point for potential therapeutic intervention, making membrane protein targets drug, as for example, in cancer research (Harvey et al., 2001). In plant cells, the signaling processes that control responses to abiotic and biotic stresses also occur at the level of MP. In fact, both in animal and plant cells, the MP controls many primary functions such as ion and metabolites transport, endocytosis, cell proliferation . . . etc. All these processes involve a wide range of highly variable protein in terms of structure and function.

This large variability in the nature of membrane proteins determine that the number of extracting processes is both extensive and specific. Thus, besides the wide range of molecular weights and isoelectric points, membrane proteins differ in their hydrophobicity and variability of surrounding lipid. This makes them difficult to remove and purify, especially in the case of protein with several transmembrane domains embedded in the lipid phase of the membrane.

Therefore, the use of membrane vesicles containing a protein of interest and maintaining its functionality and properties, can provide many advantages in terms of stability and reducing economic costs production.

Movements of almost all solutes through the membrane are mediated by membrane transport proteins, which are more or less specialized in transport specific molecules. Since diversity and physiology of different cells of an organism is widely related to its ability to capture some or other external elements, it is postulated that there must be a pool of specific transport proteins for each cell type and for each specific physiological moment (Lodish et al., 2005). This differential expression is regulated by: differential transcription of the encoding genes for these proteins and their translation.

These are transmembrane proteins that possess many alpha helices immersed in the lipid matrix. This structure is likely to involve a pathway through protein hydrophilic environments that would produce a disruption in the highly hydrophobic lipids medium (Lodish et al., 2005). These proteins are involved in the transport pathways: they act as both ATP-driven pumps, energy metabolism dependent or as passive channels.

Some of these proteins are able to transport, water, ions and small solutes, like glycerol and urea, both hygroscopic agents widely used in cosmetics.

The fact that integral membrane proteins are minor constituents compared to other cellular soluble proteins is an additional problem to the extraction. So far, extracting these functional proteins has been achieved when inserted into the lipid bilayer. Also, extraction of hydrophobic proteins from plasma membrane fractions with a higher yield by modifying the method of extraction has been achieved (Gerbeau et al., 2002). However, a stimulatory method (also called "elicitor") of the intrinsic protein, combined with suitable extraction protocol of plasma membrane vesicles, increases the yield of plant vesicles containing membrane proteins.

Liposomes have been considered as the most innovative contribution in dermatology pharmaceutical and cosmetic areas. However, due to their high cost, their variable phospholipids purity and its instability, the surfactants containing vesicles represent an advantageous alternative. Furthermore, these vesicles contain intrinsic membrane proteins able to act as transporters of substances.

Some of the therapeutic and cosmetic substances have been used in vehicle systems are:

| Name of the therapeutic agent. | Therapeutic category | Reference |
| --- | --- | --- |
| Levonorgestrel | Contraceptive | Jain N K et al., 1998 |
| Flurbiprofen | Non-steroidal anti-inflammatory (NSAIDs) | Mokhtar et al., 2008 |
| Captopril | Anti-hypertensive | Gupta et al., 2007 |
| Estradiol | Female hormone | Tsai et al., 2001 |
| Ketorolac tromethamine | (NSAIDs) | Alsarra et al., 2005 |
| Furosemide | Diuretic | Azeem et al., 2008 |
| Losartan potassium | Anti-hypertensive | Thakur et al., 2009 |
| Chlorpheniramine maleate | Antihistamine | Varshosaz et al., 2005 |
| Pseudo-ceramide | Anti-wrinkle | Iwai et al., 1998 |
| Benzofenone-4/Octylmethoxycinnamate | Sun protection | Brinon et al., 1999 |
| Vitamin A | Antioxidant | Cioca et al., 1991 |

Extraction of membrane vesicles is achieved by the use of the two-phase polymer system (Larsson et al., 1987) that can separate the plasma membrane fraction from the rest of the microsomal fraction. For that, the procedure consists in the cold homogenization and separation in dextran/polyethylene glycol.

Plant peptide hydrolyzes has been used: *Brassica napus* (FR2925325), *Triticummonoccocum* (FR2925327), *Zea mays* L. (FR2925326), *Triticumturgidum* (FR2925328), *Solanumtuberosum* (FR2925330), *Avena sativa* L. (FR292532), *Viciafaba* L. (FR2925331), for activating the synthesis of aquaporins present in the human epidermis (mainly AQP3), either alone or in combination with other active ingredients. AQP3 is present in the plasma membrane of keratinocytes in the epidermis (Sougrat et al., 2002) and plays an important role in controlling water flow through the skin. Thus, these AQP3 can transport glycerol which is involved in the formation of the hydrolipidlayer that maintains the flexibility and sensory qualities of the stratum corneum. Hydration and amount of AQP3 in keratinocyte are both related in terms that an increase of AQP3 content the skin improves the epidermis hydration (Dumas et al., 2007).

However, the discovery that skin carcinoma cells highly overexpress human AQP3 aquaporin (Hara-Chikuma and Verkman 2008b) suggests caution in the use of modulators of the aquaporin expression to promote skin hydration.

An alternative to the use of ingredients for activating the synthesis of aquaporins is the use of natural vesicles enriched in both aquaporins and other membrane proteins that would be used as the lipid vehicle in the release of water or other substances in the epidermis.

Aquaporins are also incorporated into cosmetic formulations (FR20010013463), determining the pharmaceutical formulation for topical use in the form of aqueous or oily solution. However, the use of membrane vesicles of natural origin (plant) which also includes other membrane transport proteins, bioactive compounds or hygroscopic agents has not been included in such a formulation, and comprises the basis of this invention. The family Brassicaceae (also called Cruciferae or cruciferous family) comprises up to 3500 plant species. Several epidemiological studies indicate that cruciferous including broccoli (*Brassica oleracea*) are a rich source of bioactive secondary metabolism like nitrogen-sulfur glucosinolates, phenolic natural antioxidants (flavonoids, anthocyanins and phenolic acids), vitamins (C, E, A, K, etc.) and minerals (nitrogen, phosphorus, potassium, calcium, iron, manganese, magnesium, zinc, copper, selenium, etc.). (Fahey et al. 2001; Moreno et al. 2006).

The plant components are also used in the cosmetic industry, for example, the use of extracts of shoots or sprouts of different fruits, berries and cruciferous vegetables, including broccoli, with applications in lotions, massage creams, nutritive creams, gels, anti-aging, detoxify or in relation to the treatment of diseases associated with the skin (US2009/0306219). Also, the vegetables and bioactive compounds, including broccoli, as an additive in anti-aging formulations, which in some cases represent 0.1 to 10% of vegetable extract solids weight incorporated into powders, pills, capsules or oily precipitates (U.S. 2009/0324522).

Some of these bioactive compounds can be incorporated into lipid vesicles for later release into the epidermis.

REFERENCES

Dumas et al. 2007. J. Drugs Dermatol., (6 Suppl):s20-4.
Fahey et al. 2001. Phytochemistry 56, 5-51.
Gerbeau et al. 2002. Plant J. 30, 71-8.
Hara-Chikuma and Verkman. 2008b. Molecular and Cellular Biology 28, 326-332.
Harvey et al. 2001. Physiol. Genomics 5, 129-136.
Larsson et al. 1987. Methods Enzymol. 148, 558-568.
Lodish et al. 2005. *Biologí a celular y molecular*. Buenos Aires: Médica Panamericana. *ISBN* 950-06-1974-3
Moreno et al. 2006. J. Pharmaceutical Biomedical Analysis 41:1508-1522
Sougrat et al. 2002. J. Invest. Dermatol. 118, 678-85.
Jain N K, Khopade A J, Vora B. J Control Release 1998, 54, 149-165.
Mokhtar M, Sammour O A, Hammad M A, Megrab N A. Int J Pharm 2008 361, 104-111.
Gupta A, Prajapati S K, Balamurugan M, Singh M, Bhatia D. Trop J Pharm Res 2007, 6, 687-693.
Tsai Y H, Fang J Y, Yu S Y, Wu P C, Huang Y B. Int J Pharm 2001, 215, 91-99.
Alsarra I A, Bosela A A, Ahmed S M, Mahrous G M. Eur J Pharm Biopharm 2005, 59, 485-490.
Azeem A, Jain N, Iqbal Z, Ahmad F J, Aqil M, Talegaonkar S. Pharm DevTechnol 2008, 13, 155-163.
Thakur R, Anwer M K, Shams M S, Ali A, Khar R K, Shakeel F, Taha. J Drug Target 2009, 17, 442-449.
Varshosaz J, Pardakhty A, Mohsen S, Baharanchi H. Drug Deliv 2005, 12, 75-82.
Iwai H, Fukasava J, Suzuki T. Int J Cosmet Sci 1998, 20(2), 87-102.
Brinon L, Geiger S, Alard V, Doucet J, Tranchant J F, Couarraze G. J Control release. 1999, 60, 67-76.
Cioca, G., James, A. H., Manuel, L. T., Herstein, M., Walter, P.: U.S. Pat. No. 4,999,348 (1991).

DESCRIPTION OF THE INVENTION

The present invention refers to a procedure for obtaining plant-plasma membrane vesicles (derived from *brassica*), enriched in aquaporins and other membrane transport proteins, which in turn could contain other substances such as natural bioactive compounds, hygroscopic or chemical agents for pharmacological and therapeutic uses.

A first aspect of the present invention is related to the methodology for increasing the amount of intrinsic membrane proteins-associated with solutes and water permeability of the plant-derived membrane.

A second aspect of the invention refers to membrane vesicles produced according to the above methodology, which comprises an effective amount of membrane proteins for different uses.

A third aspect is referred to the application fields of the plasma membrane vesicles to alow water or other substances delivery/release into the epidermis.

Specifically, in a first aspect, the present invention is referred to a methodology for obtaining plant-plasma membrane vesicles enriched in intrinsic membrane transport proteins comprised by:

A first phase of stimulation (or elicitation), applying a combined process of both abiotic stress and a bioactive compound to the plant.

A second step comprises membrane vesicles extraction.

From now on, the aquaporins and other membrane transport proteins enrichment procedure in plant-vesicles will be named "procedure of the invention".

Preferably, the procedure of the invention comprises a method of stimulation that involves a membrane protein increase in the whole plant, or in parts of the plant, such as leaves, stem, root and inflorescences which will be used as original plant material for the membrane vesicles extraction or any combinations thereof.

Therefore, the vesicles extraction can be obtained from whole plants or parts of the plants selected from root, stem, leaves, inflorescences or possible combinations of these parts, from different vegetables, preferably Brassicaceae family (also known as Cruciferae), family of crucifers, and preferred *Brassica* spp. Thus, one preferred fulfillment is the procedure of the invention where the plant belongs to the Brassicaceae family.

Vegetables are selected from turnip, cress, radish, kohlrabi, cabbage, red cabbages, rutabaga, Brussels sprouts, mustards, different varieties of broccoli (brocolini, broccoli, romanesco broccoli, white or purple broccoli, etc.) as well as other root, leaf or inflorescence vegetables such as sage, fenugreek, onion or garlic, and it may contain any of their health-promoting phytochemicals and nutrients. In one realization even more preferred, the plant is broccoli.

In the present invention, broccoli, is understood as any variety of *Brassica oleracea*[Italica group], developed in any type of growth and environmental conditions and that may be enriched in a mineral rich medium with controlled agronomical conditions that would increase its intrinsic aquaporin expression.

The procedure of the invention comprises stimulation through a bioactive compound, a vitamin, a phenolic compound, a glucosinolate, an extract enriched in at least one of these compounds or a combination of at least two of them. In a preferred realization, the application time of the bioactive compound varies between 1 and 78 hours, both limits included. Preferably, the concentration reached in the irrigation water varies between 5 and 100 µM, both limits included.

Furthermore, the plant is subjected to abiotic stress together with the application of the bioactive compound, preferably modifying the electrical conductivity (EC) of the irrigation water, comprising the addition of an osmotic stress substance to the plant-solution irrigation which temperature is more preferably between 15 and 35° C., both limits included. In other words, the bioactive compound is further applied when the electrical conductivity of the plant irrigation water was previously increased, ranging from 0.5 to 6 dS m$^{-1}$, both limits included. It was achieved after the addition of an osmotic stress substance (in mM concentration), preferably in a concentration between 10 and 80 mM combined with different temperature range in the irrigation tanks, preferably between 0 and 10° C., around the average ambient temperature of 25° C., since the electrical conductivity of a solution increases about 2% every temperature degree rise. In a preferred realization, the osmotic stress substance is selected from: $CaCl_2$, NaCl, KCl, $Na_2SO_4$, $K_2SO_4$, $(NH_4)_2SO_4$, $MgSO_4$, $KNO_3$, $NH_4NO_3$, $Mg(NO_3)_2$, $Ca(NO_3)_2$, $KH_2PO_4$, $NH_4H_2PO_4$, mannitol, sorbitol, polyethylene glycol and combinations of these compounds.

The vesicle extraction was carried out according to the technique of Larsson et al., 1987, which is incorporated in the reference list. However, the methodology included some modifications which make the process suitable for industry, because of the lower costs and shorter time extraction. Thus, instead of vacuum filtration and manual homogenization it was employed a homogenizer system with automatic mechanical homogenization under cold (4-10° C.), polytron type or mechanical mixer (Thermomix) with different combinations of speed and time. In other words, this means that the second stage of the process of the invention, referred to the extraction of membrane vesicles, comprising at least one step of mechanical homogenization with a homogenizer. Homogenization speed varied from 0 to 5000 rpm, with an initial time-course from 0 to 1 min and a speed of 1000-4000 rpm and a second homogenization step from 0 to 25 s with a speed of 3000-5000 rpm. Also, the conservation buffer was modified in order to eliminate those compounds that may result toxic or harmful to human health, such as PIPES buffer, described in the published extraction method, that is absorbed through the skin and was replaced by another buffer from the following: bicarbonate buffer, phosphate buffer and acetate buffer at the same concentration and pH. Therefore, the extraction of membrane vesicles according to the invention comprises resuspending the extracted vesicles in a conservation buffer selected from phosphate, bicarbonate and acetate buffer.

A second aspect of the invention referred to membrane vesicles obtained according to the conditions described above comprising an effective amount of membrane transport proteins.

In the present invention, an "effective amount" is understood as the quantity of membrane proteins into vesicles obtained by the process of the invention enough to have efficacy at hydration/health level for both humans and animals, and applicable to dermatological, pharmacological or therapeutic purposes.

A third aspect of the present invention is referred to the use of membrane vesicles enriched with membrane transport proteins for industrial and commercial purposes, since they may be a natural carrier/vehicle for the release/delivery of water, bioactive substances, hygroscopic agents, salts and other chemicals such as antibiotics or any formulation for cosmetic or therapeutic uses. That is, these vesicles may be applied for dermatological, pharmacological or therapeutic purposes, incorporating therein additional substances, preferably a natural bioactive compound, hygroscopic agent, a chemical or any possible combination of these substances.

In the treatment of a pathophysiological process, it is desirable that the drug delivery is performed such that the drug reaches its site of action at a certain concentration. Liposomes have been used as vectors of drug and glycoproteins among others, which have the advantage of being biodegradable and endocytosis susceptible.

Liposomes are microscopic vesicles constituted by concentric phospholipid bilayers with aqueous compartments which are able to capture a variety of hygroscopic active substances, liposoluble or amphiphilic.

Therefore, this invention refers to the use of plant-plasma membrane vesicles as transport systems or vectors for specific substances release for topical application or therapeutic uses.

These vesicles contain membrane transport proteins in their structure allowing the release of water, ions and other substances such as ammonia, low molecular weight sugars, glucosinolates, urea and glycerol (hydration agents) that can be transported through the membrane proteins and therefore uses for cosmetic or dermatology, hydration or stitches cure, burns and other injuries.

Furthermore, the invention refers to the use of membrane vesicles containing plant derived bioactive substances (vitamin C, glucosinolates, or phenolic compounds) with antioxidant capacity to use them in cosmetic formulations.

Another aspect of the invention refers to a vesicle obtained by the process of the invention, comprising an effective amount of membrane transport intrinsic proteins, which acts as a carrier and stabilizer of at least one of the above bioactive compounds in a liquid formulation or drink (a liquid food such as milk or juice). In the present invention it has been found that the vesicles obtained following the procedure of the invention increased the stability of bioactive compounds such as glucosinolates in liquid formulations, as shown in the Example 5.

FIGURE DESCRIPTIONS

FIG. 1. Immunodetection by Western-blotting. Signal intensity for a plasma membrane protein (aquaporins) was showed in control plants and plants exposed to the stimulation methodology (elicitation) of the invention.

Figure 2:
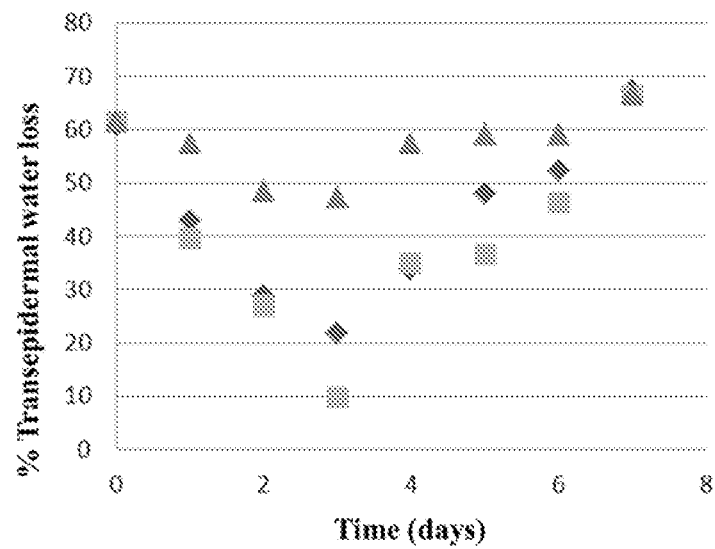

FIG. 2. Comparative hydration of the vesicles with and without hygroscopic agent. Plasma membrane protein concentration in the vesicles application was 2 μg μL$^{-1}$. ■ Vesicles application with hygroscopic agent; ♦ Vesicles application without hygroscopic agent; ▲ Direct application of the hygroscopic agent without vesicles.

Figure 3:
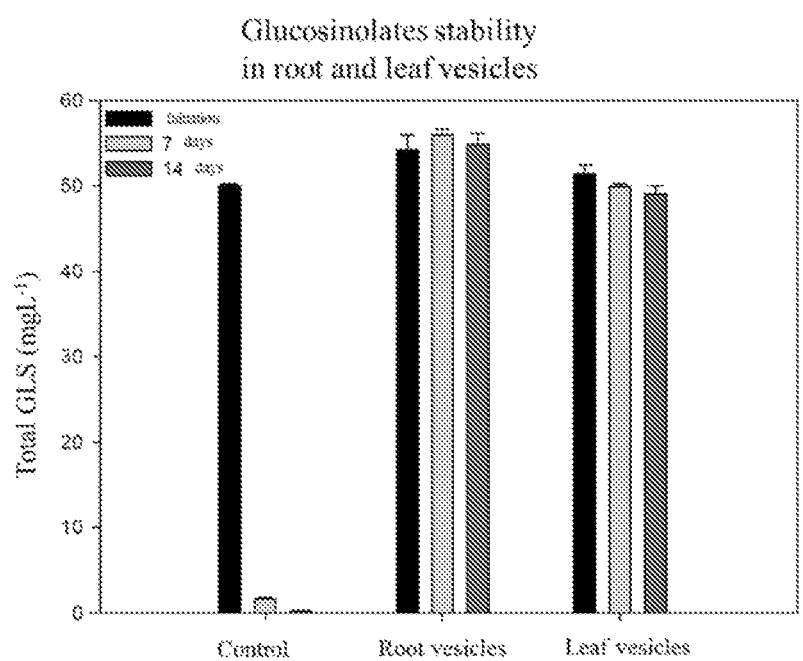

FIG. 3. Total glucosinolates stability in plasma membrane vesicles derived from broccoli root and leaf (n=3).

Figure 4:
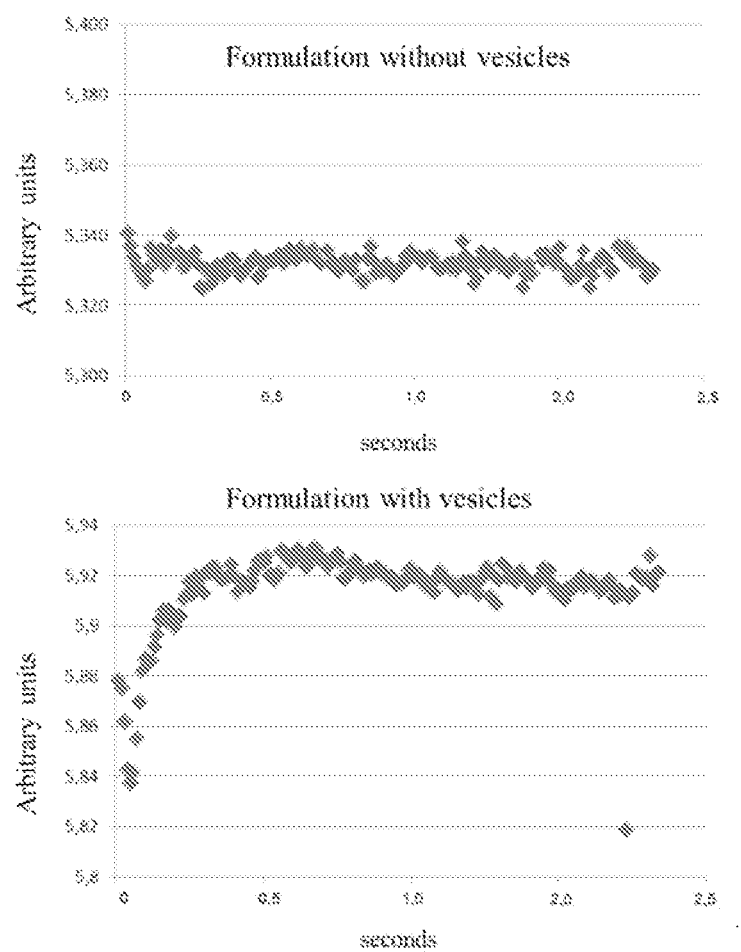

FIG. 4. Plasma membrane vesicles functionality derived from broccoli root in a cosmetic formulation. Measurements were made at 5 days, 1 month and 6 months after sample preparation.

Figure 5:
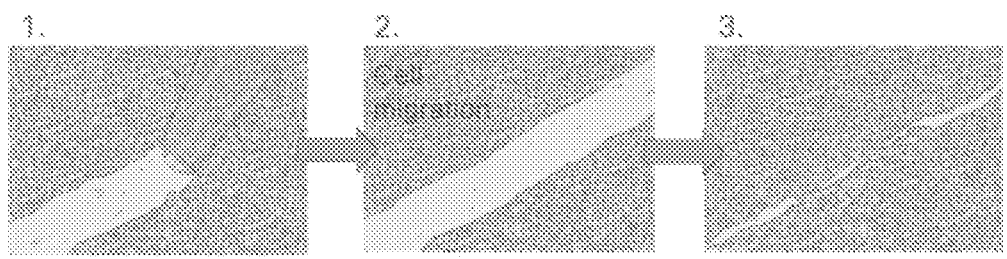

FIG. 5. Representation of wound healing assay by scrapping on cell layer. 1: Performing a uniform scraping cell to create an empty space without cells. 2: Migration of cells into the empty space generated in 1. 3: Cellular invasion of the empty space generated in 1.

Figure 6:
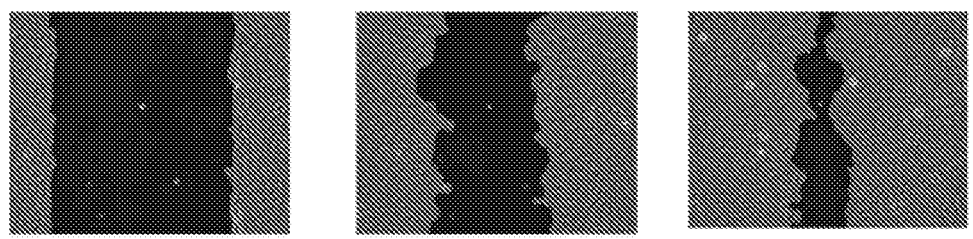

FIG. 6. Evolution of cellular healing assay with a human keratinocytes (HaCaT) layer incubated in the presence of vesicles with glucosinolates. Images were taken after removing the cell layer and after 0 hours (left), 8 hours (center) and 16 hours (right) incubation in the presence of the vesicles with glucosinolates.

Figure 7:
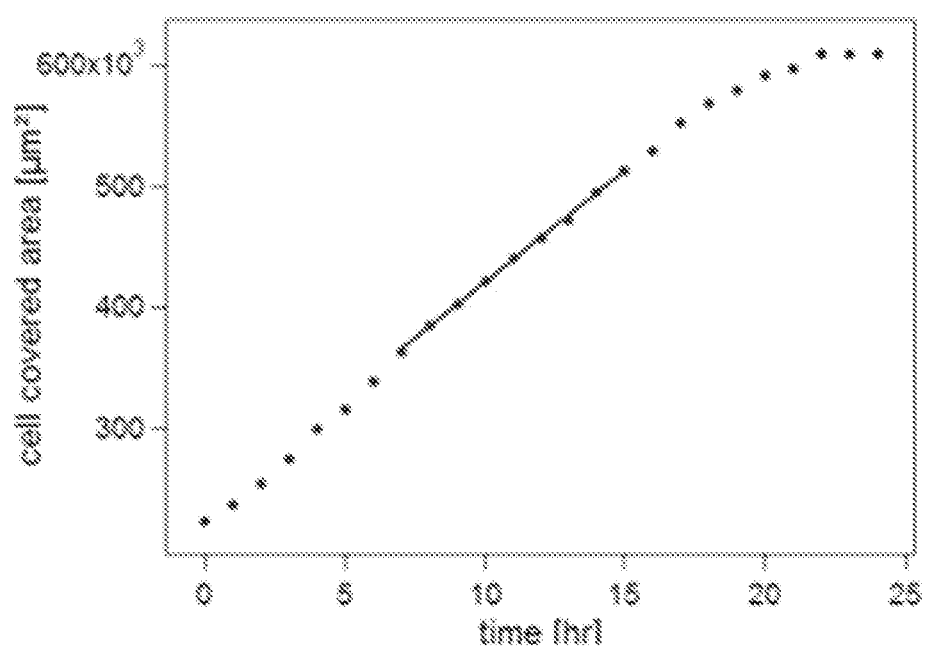

FIG. 7. Graphical representation of cell occupation area lacking of human keratinocyte (HaCaT) versus incubation time (in hours) in the presence of vesicles containing glucosinolates. The slope of the straight line indicates the area occupancy rate expressed in μm$^2$/h.

Figure 8:
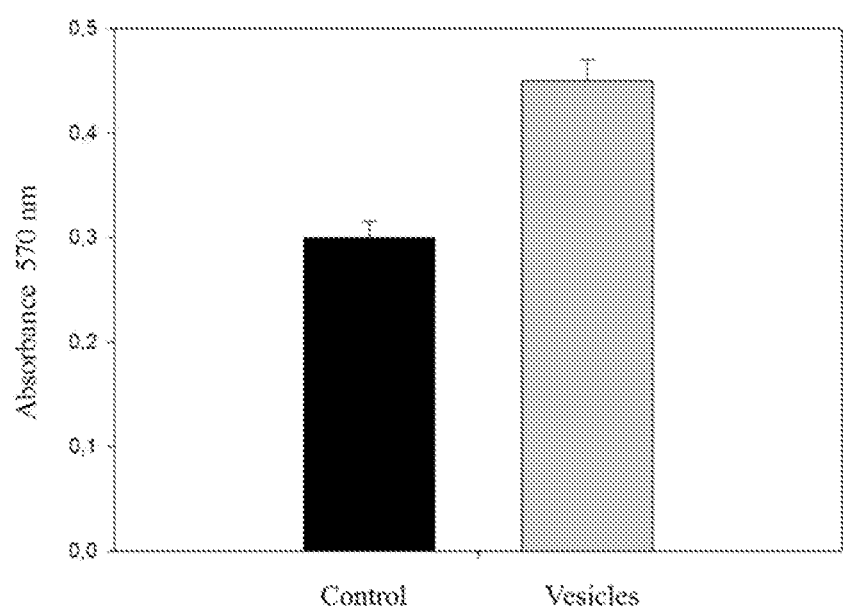

FIG. 8. Comparison of HaCaT cell growth with and without plasma membrane vesicles from root (n=3).

Figure 9:
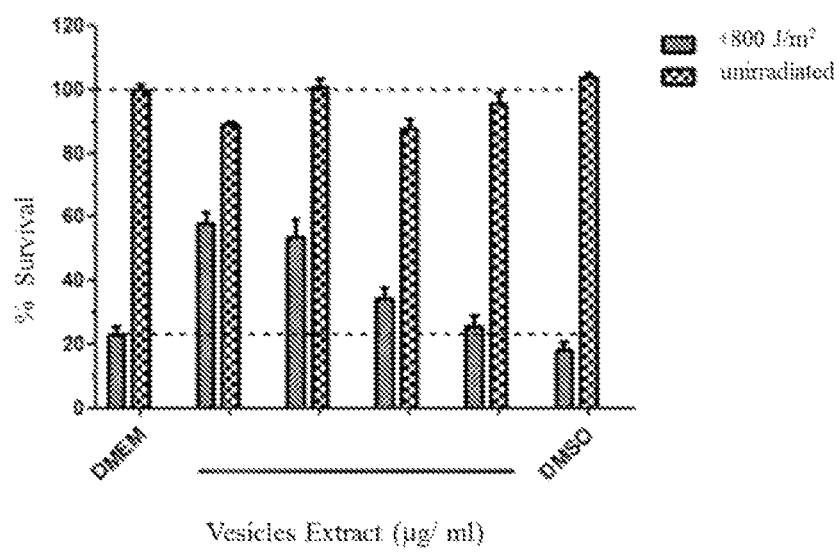

FIG. 9. Survival percentage of human keratinocytes (HaCaT) treated with a dose of 800 J/m2 UVB in the presence of different concentrations of containing glucosinolates vesicles, incubated for 72 h. A protective effect on the cells depending on the extract concentration was observed.

Figure 10:
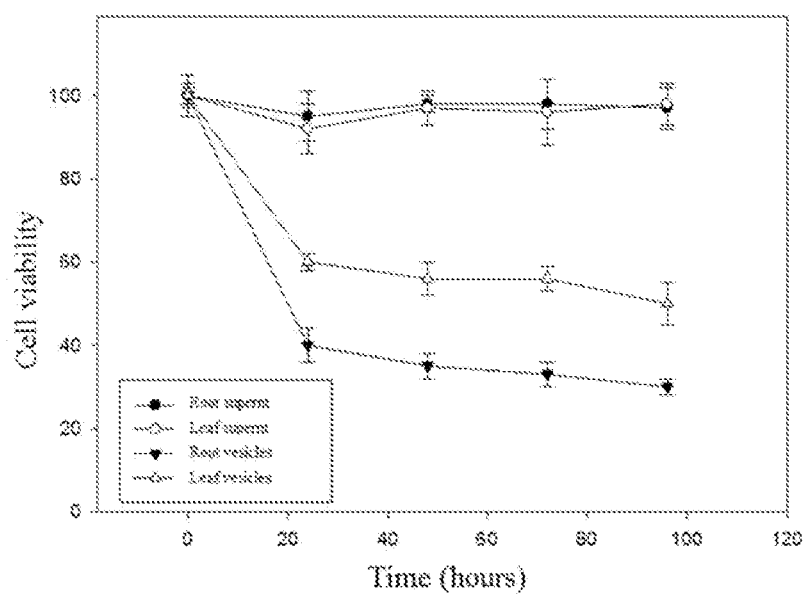

FIG. 10. B16 cell cytotoxicity solutions of glucosinolates in the supernatant of the mixture of plasma membrane vesicles derived from leaf and root compared to broccoli vesicles containing glucosinolates (n=3).

EXAMPLE 1

Stimulation Procedure of Plant-Membrane Proteins (FIG. 1)

The method of the invention comprises stimulation through a bioactive compound, an aliphatic glucosinolate such as sinigrin, which was added to the irrigation water at the concentration of 50 µM for 24 hours in the broccoli cultivation. Previous to the compound addition the electrical conductivity (EC) of the irrigation water was modified, increasing to 6 dS m$^{-1}$ after the application of an osmotic stress substance such as 40 mMKCl. Protein extraction was automatically preformed from leaf tissue (20 g) using a polytron, in a first step of homogenization, during 15 s at 4000 rpm and a second step of 20 s at 5000 rpm. The extraction buffer containing 50 mM HEPES and 0.5 M (pH 7.5) mannitol, to this solution was then added 1 mM dithiothreitol (DTT), 5 mM ascorbic acid and 0.6% (w/v) insoluble polyvinylpyrrolidone (PVP), 10% glycerol and 5 mM β-glycerolphosphate. The homogenate was centrifuged at 10.000 g for 20 minutes at 4° C. and the supernatant was collected and centrifuged at 55.000 g for 35 min at 4° C. The pellet was re-suspended in a buffer (0.3 M mannitol, 5 mM bicarbonate buffer at pH 7.0-8.0).

The suspension was added to a polymer system with a dual phase 6.0% (w/v) Dextran T500 (Pharmacia), 6.0% (w/v) polyethylene glycol (PEG) 3350 (Sigma), 3 mMKCl, 5 mM phosphate buffer (pH 7.8) and 0.33 M mannitol or sucrose The phase system was centrifuged at 4000 g for 5 min at 4° C. The upper phase which collects the plasma membrane was diluted in a new buffer. In the storage buffer 10 mM bicarbonate buffer at pH 8.3 with 0.33 M sucrose.

EXAMPLE 2

Efficiency of the Extraction from Brassica Cultivar

The yield of the plasma membrane vesicles extraction was evaluated for Brassica regarding other cultivars. In the table 1, the protein content of the membrane vesicles for different plants is showed. Brassica growing after stimulation resulted in larger amount of plasma membrane protein. The table indicates the amount of protein expressed in µg µL$^{1}$. The yield of the process is higher than that obtained for other cultivars even vesicles isolated from Beta vulgaris since the amount of starting plant material was higher. Furthermore, considering that mechanical extraction involves a loss of performance, protein levels remain above the majority of plants by applying a methodology able to be scaled at industrial level.

TABLE 1

Comparison of the concentration of plasma membrane protein (object of the invention) present in plant membrane vesicles*. The concentration was obtained after plant stimulation and mechanical extraction.

|  | Capsicum annuum | Lycopersicum esculentum | Zea mays | Beta vulgaris | Brassica oleracea | *Brassica oleracea + stimulation |
|---|---|---|---|---|---|---|
| Starting Plant Material (g) | 18 | 25 | 18 | 150 | 20 | 20 |
| Homogenization | manual | manual | manual | manual | manual | mechanical |
| Plasma MembraneProtein (µg µL$^{-1}$) | 1.32 | 1.98 | 2.79 | 9.16 | 3.06 | 3.51-5.0 |

Table 2 shows a list of membrane proteins identified by HPLC-MS-MS in Brassica oleracea varItalica.

TABLE 2

Membrane transport proteins identified in the plasma membrane vesicles from Brassica oleraceavarItalica after digestion with 3 different endoproteases Trypsin digestion

| Accession | #AAs | M. W[Da] | calc. pI | Description | Σcoverage |
|---|---|---|---|---|---|
| A5DXI9 | 362 | 41667.20 | 5.26 | Actin cytoskeleton-regulatory complex protein END3 OS = Lodderomyceselongisporus GN = END3 PE = 3 SV = 1 - [END3_LODEL] | 3.87 |
| P92935 | 618 | 67485.82 | 9.48 | ADP, ATP carrier protein 2, chloroplastic OS = Arabidopsis thaliana GN = AATP2 PE = 1 SV = 2 - [TLC2_ARATH] | 1.94 |
| P61837 | 286 | 30668.98 | 9.01 | Aquaporin PIP1-1 OS = Arabidopsis thaliana GN = PIP1-1 PE = 1 SV = 1 - [PIP11_ARATH] | 16.08 |

TABLE 2-continued

Membrane transport proteins identified in the plasma membrane vesicles from *Brassica oleraceavarltalica* after digestion with 3 different endoproteases
Trypsin digestion

| Accession | #AAs | M. W[Da] | calc. pI | Description | Σcoverage |
|---|---|---|---|---|---|
| Q06611 | 286 | 30578.01 | 9.03 | Aquaporin PIP1-2 OS = *Arabidopsis thaliana* GN = PIP1-2 PE = 1 SV = 1 - [PIP12_ARATH] | 9.79 |
| P30302 | 285 | 30409.69 | 7.84 | Aquaporin PIP2-3 OS = *Arabidopsis thaliana* GN = PIP2-3 PE = 1 SV = 1 - [PIP23_ARATH] | 3.86 |
| P19456 | 948 | 104334.99 | 6.99 | ATPase 2, plasma membrane-type OS = *Arabidopsis thaliana* GN = AHA2 PE = 1 SV = 2 - [PMA2_ARATH] | 4.64 |
| Q42556 | 954 | 105141.76 | 6.39 | ATPase 9, plasma membrane-type OS = *Arabidopsis thaliana* GN = AHA9 PE = 2 SV = 2 - [PMA9_ARATH] | 2.41 |
| O80899 | 757 | 84206.29 | 7.21 | Cellulose synthase-like protein B2 OS = *Arabidopsis thaliana* GN = CSLB2 PE = 2 SV = 1 - [CSLB2_ARATH] | 1.72 |
| Q9SAE4 | 490 | 55969.76 | 7.99 | Cytochrome P450 71B29 OS = *Arabidopsis thaliana* GN = CYP71B29 PE = 2 SV = 1 - [C71BT_ARATH] | 2.65 |
| O65782 | 499 | 56809.55 | 8.37 | Cytochrome P450 83B1 OS = *Arabidopsis thaliana* GN = CYP83B1 PE = 1 SV = 1 - [C83B1_ARATH] | 2.40 |
| P0C7R4 | 658 | 73842.98 | 7.68 | Pentatricopeptide repeat-containing protein At1g69290 OS = *Arabidopsis thaliana* GN = At1g69290 PE = 2 SV = 1 - [PP110_ARATH] | 1.98 |
| P46032 | 585 | 64379.59 | 5.67 | Peptide transporter PTR2 OS = *Arabidopsis thaliana* GN = PTR2 PE = 1 SV = 1 - [PTR2_ARATH] | 2.22 |
| Q8RY89 | 769 | 87347.74 | 8.68 | Phosphatidylinositol-4-phosphate 5-kinase 8 OS = *Arabidopsis thaliana* GN = PIP5K8 PE = 2 SV = 1 - [PI5K8_ARATH] | 2.60 |
| P83970 | 951 | 104618.27 | 6.81 | Plasma membraneATPase OS = *Triticumaestivum* GN = ha1 PE = 2 SV = 1 - [PMA1_WHEAT] | 2.42 |
| Q9ZVX8 | 278 | 29481.38 | 8.85 | Probable aquaporin PIP2-8 OS = *Arabidopsis thaliana* GN = PIP2-8 PE = 2 SV = 1 - [PIP28_ARATH] | 4.32 |
| O82226 | 747 | 85386.45 | 9.28 | Probable cyclic nucleotide-gated ion channel 6 OS = *Arabidopsis thaliana* GN = CNGC6 PE = 1 SV = 2 - [CNGC6_ARATH]] | 1.87 |
| Q8LGI2 | 454 | 49649.88 | 8.29 | Probable mitochondrial saccharopine dehydrogenase At5g39410 OS = *Arabidopsis thaliana* GN = At5g39410 PE = 1 SV = 2 - [SCPDH_ARATH] | 2.20 |
| A3LPW2 | 511 | 59735.82 | 8.63 | Protein FYV10 OS = *Pichiastipitis* GN = FYV10 PE = 3 SV = 2 - [FYV10_PICST]] | 1.96 |
| Q9M088 | 484 | 52681.84 | 6.18 | Putative glucan endo-1,3-beta-glucosidase 5 OS = *Arabidopsis thaliana* GN = At4g31140 PE = 1 SV = 1 - [E135_ARATH] | 2.27 |
| Q944A7 | 512 | 56781.73 | 5.78 | Putative serine/threonine-protein kinase At4g35230 OS = *Arabidopsis thaliana* GN = At4g35230 PE = 1 SV = 1 - [Y4523_ARATH] | 8.01 |
| Q9FHD7 | 487 | 54590.20 | 6.33 | Probable serina/treonina-protein kinasa At5g41260 OS = *Arabidopsis thaliana* GN = At5g41260 PE = 1 SV = 1 - [Y5126_ARATH] | 3.70 |
| Q96704 | 349 | 39206.65 | 8.46 | Replication-associated protein OS = Cabbage leaf curl virus (isolate Jamaica) GN = AC1 PE = 3 SV = 2 - [REP_CALCV] | 4.01 |
| P23586 | 522 | 57572.98 | 8.94 | Sugar transport protein 1 OS = *Arabidopsis thaliana* GN = STP1 PE = 1 SV = 2 - [STP1_ARATH] | 2.30 |
| Q9SZN1 | 487 | 54270.67 | 5.15 | V-type proton ATPase subunit B2 OS = *Arabidopsis thaliana* GN = VHA-B2 | 2.87 |

TABLE 2-continued

Membrane transport proteins identified in the plasma membrane vesicles from
*Brassica oleraceavarItalica* after digestion with 3 different endoproteases
Trypsin digestion

| Accession | #AAs | M. W[Da] | calc. pI | Description | Σcoverage |
|---|---|---|---|---|---|
| | | | | PE = 2 SV = 1 - [VATB2_ARATH] SV = 1 - [VATB2_ARATH] | |

Digestion with Glu-C

| Accession | #AAs | M. W[Da] | calc. pI | Description | Σcoverage |
|---|---|---|---|---|---|
| Q43291 | 164 | 18641.07 | 10.46 | 60S ribosomal protein L21-1 OS = *Arabidopsis thaliana* GN = RPL21A PE = 2 SV = 2 - [RL211_ARATH] | 10.37 |
| Q08733 | 286 | 30612.94 | 8.85 | Aquaporin PIP1-3 OS = *Arabidopsis thaliana* GN = PIP1-3 PE = 1 SV = 1 - [PIP13_ARATH] | 3.85 |
| O81108 | 1014 | 110368.25 | 5.68 | Calcium-transporting ATPase 2, plasma membrane-type OS = *Arabidopsis thaliana* GN = ACA2 PE = 1 SV = 1 - [ACA2_ARATH] | 1.68 |
| P23980 | 704 | 77990.52 | 8.81 | Plasma membraneATPase 2 (Fragment) OS = *Solanumlycopersicum* GN = LHA2 PE = 3 SV = 1 - [PMA2_SOLLC] | 1.99 |
| Q8VZU2 | 304 | 34203.93 | 6.44 | Syntaxin-132 OS = *Arabidopsis thaliana* GN = SYP132 PE = 1 SV = 1 - [SY132_ARATH] | 5.59 |

Digestion with Lys.

| Accession | #AAs | M. W[Da] | calc. pI | Description | Σcoverage |
|---|---|---|---|---|---|
| P42739 | 76 | 8535.58 | 7.25 | Ubiquitin OS = *Acetabularia cliftonii* PE = 3 SV = 1 - [UBIQ_ACECL] | 21.05 |
| P61837 | 286 | 30668.98 | 9.01 | Aquaporin PIP1-1 OS = *Arabidopsis thaliana* GN = PIP1-1 PE = 1 SV = 1 - [PIP11_ARATH] | 16.43 |
| Q08733 | 286 | 30612.94 | 8.85 | Aquaporin PIP1-3 OS = *Arabidopsis thaliana* GN = PIP1-3 PE = 1 SV = 1 - [PIP13_ARATH] | 10.14 |
| Q39571 | 203 | 22584.49 | 6.21 | GTP-binding protein YPTC1 OS = *Chlamydomonasreinhardtii* GN = YPTC1 PE = 3 SV = 1 - [YPTC1_CHLRE] | 7.88 |
| Q9SIH4 | 206 | 21955.77 | 8.29 | UPF0497 membrane protein At2g36100 OS = *Arabidopsis thaliana* GN = At2g36100 PE = 2 SV = 1 - [U4979_ARATH] | 7.28 |
| Q42962 | 401 | 42337.62 | 5.97 | Phosphoglycerate kinase, cytosolic OS = *Nicotianatabacum* PE = 2 SV = 1 - [PGKY_TOBAC] | 4.24 |
| P30302 | 285 | 30409.69 | 7.84 | Aquaporin PIP2-3 OS = *Arabidopsis thaliana* GN = PIP2-3 PE = 1 SV = 1 - [PIP23_ARATH] | 3.86 |
| Q944A7 | 512 | 56781.73 | 5.78 | Putative serine/threonine-protein kinase At4g35230 OS = *Arabidopsis thaliana* GN = At4g35230 PE = 1 SV = 1 - [Y4523_ARATH] | 3.52 |
| Q42479 | 529 | 59298.66 | 6.37 | Calcium-dependent protein kinase 3 OS = *Arabidopsis thaliana* GN = CPK3 PE = 1 SV = 1 - [CDPK3_ARATH] | 2.84 |
| O48639 | 521 | 57219.68 | 9.01 | Probable inorganic phosphate transporter 1-3 OS = *Arabidopsis thaliana* GN = PHT1-3 PE = 2 SV = 1 - [PHT13_ARATH] | 2.50 |
| Q43128 | 947 | 104748.96 | 6.43 | ATPase 10, plasma membrane-type OS = *Arabidopsis thaliana* GN = AHA10 PE = 2 SV = 2 - [PMA10_ARATH] | 1.80 |
| P19456 | 948 | 104334.99 | 6.99 | ATPase 2, plasma membrane-type OS = *Arabidopsis thaliana* GN = AHA2 PE = 1 SV = 2 - [PMA2_ARATH] | 1.16 |

EXAMPLE 3

Hydration Test of the Vesicles on the Skin

The assay was carried out with 5 volunteers whose skin had extreme values of water loss. The process was conducted with pure vesicles at 2 $\mu g\ \mu L^{-1}$ concentration in the conservation buffer described in Example 1. A comparative study between vesicles with and without a hygroscopic agent was done. The hygroscopic agent was taken as a reference. Measurements were made every 24 h on the back hand skin. The third day the treatment was stopped.

EXAMPLE 4

Test Skin Hydration with Volunteers

The test was carried out with 15 volunteers. The vesicles were applied on the skin of the face close to the eyes. The experiment was done with vesicles diluted in the storage buffer solution (pH 6) described in Example 1 at two different concentrations 20 and 0.2 µg µL$^{-1}$. Glycerol was added (0.02%) as hygroscopic agent to the vesicles. Applications were made twice per day. Two sets of experiments were developed, short time (0 hours, 10 minutes, 1 hour, 2 hours) and long time (day 0, 2 days, 5 days and 7 days) applications. The results are shown in Tables 3 and 4.

TABLE 3

Percentage decrease in water loss from the facial skin after the application of enriched-vesicles solution extracted from broccoli leaves at concentrated and diluted (20 y 0.2 µg · µL$^{-1}$) amounts, expressed as protein concentration and glycerol as the hygroscopic agent. The experiment was done at short times and in 15 volunteers.

|  |  | % of decrease in water loss | | | |
| --- | --- | --- | --- | --- | --- |
|  |  | 0 h | 10 min | 1 h | 2 h |
| Total | Mean value | 100 | 90.05 | 84.59 | 82.12 |
|  | ±SE |  | 4.34 | 2.12 | 2.41 |
| Concentrated | Average | 100 | 91.86 | 85.00 | 83.29 |
|  | ±SE |  | 2.91 | 2.23 | 2.39 |
| Diluted | Mean value | 100 | 88.55 | 84.25 | 81.15 |
|  | ±SE |  | 5.31 | 2.11 | 2.48 |

TABLE 4

Percentage decrease in water loss from the facial skin after the application of enriched-vesicles solution extracted from broccoli leaves at concentrated and diluted (20 y 0.2 µg · µL$^{-1}$) amounts, expressed as protein concentration and glycerol as the hygroscopic agent. The experiment was done at long times and in 15 volunteers.

|  |  | % of decrease in water loss | | | |
| --- | --- | --- | --- | --- | --- |
|  |  | 0 d | 2 d | 5 d | 7 d |
| Total | Mean value | 100 | 74.35 | 64.73 | 58.72 |
|  | ±SE |  | 3.17 | 3.38 | 3.49 |
| Concentrated | Average | 100 | 77.65 | 60.63 | 53.89 |
|  | ±SE |  | 3.51 | 3.86 | 3.06 |
| Diluted | Mean value | 100 | 71.60 | 68.14 | 62.74 |
|  | ±SE |  | 2.79 | 2.75 | 3.55 |

EXAMPLE 5

Stability of Glucosinolates in Vesicles

Extracts of root and leaves membrane vesicles from broccoli plants enriched in membrane proteins (0.3 mg ml$^{-1}$ protein) were mixed with extract rich in glucosinolates obtained from broccoli seeds. Seeds of broccoli were previously washed, disinfected and dried in an oven for 24 hours at 100° C. The seeds were homogenized with 70% methanol (v/v) to obtain a puree-like homogenate. Samples were heated 70° C. for 20 min under stirring. Then, they were centrifuged (17, 500 g at 4° C.) for 15 min and evaporated with N$_2$. Finally the samples were resuspended in ultrapure water Milli-Q and filtered through 0.45 µm mesh (Millex HV13 of polietersulfane, Millipore). The mixture of vesicles with glucosinolates was ultracentrifuged to remove remaining glucosinolates not included in vesicles. The vesicles were re-suspended in the initial volume. The supernatants were considered the control. The results are shown in FIG. 3.

EXAMPLE 6

Vesicle Stability in Cosmetic Formulations

A fat-free cosmetic formulation and facial serum constituent in solution based on 0.1% of proteoglycans. This product was the basis for the addition of membrane vesicles extract from broccoli root at 0.02% concentration. The result was determined by measuring the stability of the vesicles response to osmotic pressure change means by stopped-flow method light scattering. Setting kinetics vesicle volume light scattering λex=515 nm at 90°. The measurements were performed at 20° C. in a stopped flow spectrophotometer SFM3. The solutions were diluted in the same medium. The hypoosmotic shock induced membrane dilution associated with transient opening and later balanced of the vesicles inside the extravesicular solution. K is the exponential constant which is related to the rate of shrinking.

The results are shown in FIG. 4.

EXAMPLE 7

Low Cytotoxicity in Cultured Human Keratinocytes (HaCaT). Cell Viability by the MTT Assay HaCaT cell line (from the ATCC, Rockville, Md.) was grown in DMEM medium with 10% (v/v) FBS, 1% (v/v) penicillin-streptomycin (0.1 mg/ml and 100 U/ml, respectively) CO$_2$ in a humidified atmosphere (5% v/v) at 37° C. for 24 h. The cells were trypsinizedevery three days following the manufacturers recommendations and placed in 6-well or 96 depending on the type of assay to be performed.

MTT assay was used as a simple, quantitative and reliable method to determine cell viability. Reagent MTT (3-(4,5-dimethylthiazol-2-il)-2,5-diphenyltetrazolium bromide) is reduced to formazan crystals in the mitochondria of the viable cells. After incubating the cells in the presence of the vesicles with glucosinolates for 72 h, the cells were washed with PBS and incubated with MTT for 3-4 h at 37° C. and 5% CO$_2$. After the medium was removed and 100 ul of DMSO was added to dissolve the formazan crystals which are insoluble in water. The plates were shaken for 15 min and quantifying the absorbance with a plate reader at 570 nm (SPECTROstar Omega, BMG LabTech GmbH, Offenburg, Germany). No cytotoxicity was observed for extracts containing vesicles with glucosinolates up to a protein concentration of 10 mg ml$^{-1}$.

EXAMPLE 8

Healing Assay on Cell Mat by Scraping Human Keratinocytes (Wound Healing Assay)

Healing assay on cell monolayer by scratch is a technique used to determine cell polarization, extracellular matrix remodeling and cell migration in different cell types. The test involves performing a uniform scratch confluent cell lawn directly with a handle or by an insert of defined dimensions that prevents cell growth where it is deposited and creating a "corridor" of approx. 1 mm away from cells. The invasion of the cells into the empty space can take anywhere from several hours to days depending on cell type. Using a rack and bright field microscope determines the speed with which the cells invade the empty space by measuring the area per unit time (make a video of 24 with frame intervals of 15 min) through the determination the slope of the curve.

Protocol:

a cell suspension of human keratinocytes (HaCaT) of 5×105 cells/ml and seeded in 35 mm plates at a density of 35,000 cells per well into wells containing the appropriate inserts. Cells were incubated in DMEM (Dulbecco's Modified Eagle Medium, Invitrogen) with 10% (v/v) FBS, 1% (v/v) penicillin-streptomycin (0.1 mg/ml and 100 U/ml respectively) CO2 in a humidified atmosphere (5% v/v) at 37° C. for 24 h and then removed the inserts. Were observed in cell-free streets microscope and determined the progression of cell growth for 24 h, taking a picture every 15 min. Then the area represented by the cells invaded ($\mu m^2$) with respect to time to give a growth curve as in FIG. 7. Comparing the slope of the curve obtained in the control $\mu m^2/hora$=2.4×105 (area occupation rate) with the slope of the curve obtained in the presence of vesicles with glucosinolates (0.3 mg ml$^{-1}$ protein) prepared as in Example 3. The result was an increase of the rate of occupancy area of the cells containing vesicles of 11±1% (n=3), indicating its ability healing.

EXAMPLE 9

Determination of the Skin Healing by a Proliferation Assay of Human Keratinocytes To determine the healing power of the epidermal cells, a proliferation assay in human keratinocytes (HaCaT) was performed. Keratinocytes were cultured in DMEM (Dulbecco's Modified Eagle Medium, Invitrogen), pH7.4, supplemented with 5% fetal bovine serum Invitrogen), 20 mg ml$^{-1}$ gentamicin and 350 ug ml$^{-1}$ fungizone. Vesicles enriched in membrane proteins at 0.1% of concentration were added to keratinocytes and proliferation was determined by MTT.

The results are shown in FIG. 8.

EXAMPLE 10

Protection of Human Keratinocytes (HaCaT) Against Damage Induced by UV Radiation HaCaT cell line (from the ATCC, Rockville, Md.) was grown in DMEM medium with 10% (v/v) FBS, 1% (v/v) penicillin-streptomycin (0.1 mg/ml and 100 U/ml, respectively) $CO_2$ in a humidified atmosphere (5% v/v) at 37° C. for 24 h. The cells were trypsinized every three days following the manufacturer's recommendations and seeded into 96-well plates. For treatment, the cells were maintained on the plate after sowing for 24 h. When cells reached 70-90% confluency, they were washed with PBS and treated with a thin layer of PBS containing extracts to be tested at various concentrations. The plate was then treated with UVB light source (800 J/m$^2$) using a UV radiation system (Bio-Link Crosslinker BLX-E312). Then, PBS buffer was replaced with fresh medium and incubated for 72 h. After incubating the cells in fresh medium for 72 h, washed with PBS and incubated with MTT for 3-4 h at 37° C. and 5% $CO_2$. Medium was removed and 100 ul of DMSO were added per well to dissolve the formazan crystals which are insoluble in water. The plates were shaken for 15 min and the absorbance was quantifyed using a plate reader at 570 nm (SPECTROstar Omega, BMG LabTech GmbH, Offenburg, Germany). The results are shown in FIG. 9.

EXAMPLE 11

Cytotoxicity in Murine B16 Melanoma Cells. Cell Viability by MTT Assay

Cell line with high metastatic ability, B16 (from ATCC, Rockville, Md.) were seeded and cultured with DMEM (Dulbecco's Modified Eagle Medium, Invitrogen), pH7.4, supplemented with 10% bovine serum fetal, Invitrogen), 10 mM HEPES, 100 U penicillin and 100 mg/ml streptomycin. Seeded cells were maintained in a wet oven at 37° C. and 5% $CO_2$. After incubation for 24 hours, the culture medium was replaced by new supernatant containing glucosinolates vesicles prepared as described in Example 3 at a concentration of 0.5%.

Cell viability was measured by the assay and the Trypan blue exclusion assay of lactate dehydrogenase activity (FIG. 10).

The invention claimed is:

1. A method for preparing plasma membrane vesicles enriched in intrinsic membrane proteins comprising:
    (a) irrigating a plant from the genus *Brassica* for at least 24 hours with an irrigation solution containing 10-80 mM KCl as an osmotic shock substance to produce a mixture solution;
    (b) modifying electrical conductivity of the mixture solution from 0.5 to 6 dS m$^{-1}$;
    (c) adding 5-100 µM glucosinolate sinigrin as a bioactive compound to the mixture solution and incubating for 1-78 hours;
    (d) extracting the membrane vesicles by homogenization of the mixture solution, re-suspending in a buffer solution and centrifuging to separate membrane vesicles into an upper phase;
    (e) collecting the upper phase containing the membrane vesicles and re-suspending the collected upper phase in a storage buffer selected a group consisting of a phosphate buffer, a bicarbonate buffer and an acetate buffer.

2. The method according the claim 1, wherein the bioactive compound is selected from the group consisting of a vitamin, a phenolic compound, a glucosinolate, a plant extract enriched in a vitamin, a plant extract enriched in a phenolic compound, a plant extract enriched in glucosinolate, and combinations thereof.

3. The method according to claim 1, wherein the plant is a variety of *Brassica oleracea*.

4. The method according to claim 1, wherein the membrane vesicles are extracted from a plant part selected from root, stem, leaves, inflorescence, or a combination of at least two of these parts.

* * * * *